US012774452B2

(12) United States Patent
Kim et al.

(10) Patent No.: US 12,774,452 B2
(45) Date of Patent: Oct. 27, 2026

(54) METHOD FOR PREPARING MESENCHYMAL STEM CELLS FROM HUMAN PLURIPOTENT STEM CELLS AND MESENCHYMAL STEM CELLS PREPARED THEREBY

(71) Applicant: DAEWOONG PHARMACEUTICAL CO., LTD., Hwaseong-si (KR)

(72) Inventors: Ki Nam Kim, Yongin-si (KR); Sung Hyun Choi, Anyang-si (KR); Boram Oh, Yongin-si (KR); Mi Kyung Choi, Seongnam-si (KR); Jun Kwon Cho, Seongnam-si (KR)

(73) Assignee: DAEWOONG PHARMACEUTICAL CO., LTD., Hwaseong-si (KR)

( * ) Notice: Subject to any disclaimer, the term of this patent is extended or adjusted under 35 U.S.C. 154(b) by 934 days.

(21) Appl. No.: 17/757,054

(22) PCT Filed: Dec. 9, 2020

(86) PCT No.: PCT/KR2020/017948
§ 371 (c)(1),
(2) Date: Jun. 8, 2022

(87) PCT Pub. No.: WO2021/118226
PCT Pub. Date: Jun. 17, 2021

(65) Prior Publication Data

US 2023/0014770 A1 Jan. 19, 2023

(30) Foreign Application Priority Data

Dec. 9, 2019 (KR) ........................ 10-2019-0162393

(51) Int. Cl.
*A61K 35/28* (2015.01)
*C12N 5/0775* (2010.01)

(52) U.S. Cl.
CPC ............ *C12N 5/0662* (2013.01); *A61K 35/28* (2013.01); *C12N 2500/30* (2013.01); *C12N 2500/32* (2013.01); *C12N 2500/90* (2013.01); *C12N 2500/98* (2013.01); *C12N 2506/02* (2013.01); *C12N 2506/45* (2013.01); *C12N 2533/50* (2013.01)

(58) Field of Classification Search
CPC ............ C12N 2506/45; C12N 2506/02; C12N 2500/90; C12N 2500/09; C12N 2513/00; A61K 35/28
See application file for complete search history.

(56) References Cited

FOREIGN PATENT DOCUMENTS

| | | | |
|---|---|---|---|
| CN | 107858328 | A | 3/2018 |
| EP | 2730649 | A1 | 5/2014 |
| KR | 20070075006 | A | 7/2007 |
| KR | 10-2013-0009943 | A | 1/2013 |
| KR | 20130013537 | A | 2/2013 |
| KR | 10-2013-0106432 | A | 9/2013 |
| KR | 20180067330 | A | 6/2018 |
| KR | 20180078160 | A | 7/2018 |
| KR | 10-1896803 | B1 | 9/2018 |
| KR | 10-2019-0027922 | | 3/2019 |
| RU | 2568059 | C1 | 11/2015 |
| WO | WO 2008/075378 | A2 | 6/2008 |
| WO | WO-2011052818 | A1 | 5/2011 |
| WO | WO-2011058558 | A2 | 5/2011 |

OTHER PUBLICATIONS

Zomer HD, Vidane AS, Gonçalves NN, Ambrósio CE. Mesenchymal and induced pluripotent stem cells: general insights and clinical perspectives. Stem Cells Cloning. Sep. 28, 2015;8:125-34. doi: 10.2147/SCCAA.S88036. PMID: 26451119; PMCID: PMC4592031. (Year: 2015).*

Pettinato G, Wen X, Zhang N. Engineering Strategies for the Formation of Embryoid Bodies from Human Pluripotent Stem Cells. Stem Cells Dev. Jul. 15, 2015;24(14):1595-609. doi: 10.1089/scd.2014.0427. Epub Jun. 2, 2015. PMID: 25900308; PMCID: PMC4499791. (Year: 2015).*

English translation of KR 20180067330 (Year: 2018).*

ThermoFisher Pluripotent Stem Cell protocols. (Year: 2014).*

Kurosawa H. Methods for inducing embryoid body formation: in vitro differentiation system of embryonic stem cells. J Biosci Bioeng. May 2007;103(5):389-98. doi: 10.1263/jbb.103.389. PMID: 17609152. (Year: 2007).*

(Continued)

*Primary Examiner* — Fereydoun G Sajjadi
*Assistant Examiner* — Qinhua Gu
(74) *Attorney, Agent, or Firm* — Seed Intellectual Property Law Group LLP

(57) ABSTRACT

The present invention relates to a method for preparation of mesenchymal stem cells from human pluripotent stem cells and, more particularly, to a method for preparation of mesenchymal stem cells, wherein mesenchymal stem cells differentiated from embryoid bodies of a certain size in a xeno-free and serum-free environment are prepared, whereby the mesenchymal stem cells exhibit increased safety and maintain their own characteristics for a long period of time. A method for preparation of mesenchymal stem cells from human pluripotent stem cells according to the present invention employs a feeder cell-free, xeno-free, and serum-free culture environment to solve the problem of contamination with a foreign animal-derived material and allow the preparation of highly safe mesenchymal stem cells. In addition, the method utilizes spheroidal embryoid bodies to form mature embryoid bodies uniform in shape and size, thereby improving the differentiation efficiency to mesenchymal stem cells and exhibiting an exceptional effect of stably maintaining mesenchymal stem cell characteristics even after a long-term subculture, such as 20 or more passages, through which human pluripotent stem cell-derived mesenchymal stem cells can be prepared in a large amount. Therefore, the invention is advantageous for commercializing cell therapeutic agents superb in safety and efficiency.

13 Claims, 10 Drawing Sheets

(56) References Cited

OTHER PUBLICATIONS

Lin Y, Chen G. Embryoid body formation from human pluripotent stem cells in chemically defined E8 media. Jun. 1, 2014. In: StemBook [Internet]. Cambridge (MA): Harvard Stem Cell Institute; 2008—. PMID: 28211653. (Year: 2014).*

Bobis-Wozowicz, S., "Diverse Impact of Xeno-free Conditions on Biological and Regenerative Properties of hUC-MSCs and Their Extracellular Vesicles," Journal of Molecular Medicine 95:205-220, Springer International, Germany (Feb. 2017).

Duff, S.E., et al., "CD105 is Important for Angiogenesis: Evidence and Potential Applications," FASEB Journal 17(9):984-992, Federation of American Societies for Experimental Biology, United States (Jun. 2003).

Extended European Search Report for European Application No. EP20900292, Munich, Germany, mailed on Jan. 4, 2024, 9 pages.

Gillmeister, M.P., et al., "An HPLC-MALDI MS Method For N-glycan analyses Using Smaller Size Samples: Application to Monitor Glycan Modulation By Medium Conditions," Glycoconjugate Journal 26:1135-1149, Springer, United States (Dec. 2009).

Jin, H.J., et al., "Down-regulation of CD 105 is Associated With Multi-lineage Differentiation in Human Umbilical Cord Blood-derived Mesenchymal Stem Cells," Biochemical and Biophysical Research Communications 381(4):676-681, Elsevier, United States (Apr. 2009).

Levi, B., et al., "CD105 Protein Depletion Enhances Human Adipose-derived Stromal Cell Osteogenesis Through Reduction of Transforming Growth Factor β1 (TGF-β1) Signaling," The Journal of Biological Chemistry 286(45):39497-39509, Elsevier Inc. on behalf of American Society for Biochemistry and Molecular Biology, United States (Nov. 2011).

Ma, Z., et al., "N-acetylcysteine Enhances the Therapeutic Efficacy of Bone Marrow-derived Mesenchymal Stem Cell Transplantation in Rats With Severe Acute Pancreatitis," Pancreatology 19(2):258-265, Elsevier, Netherlands (Mar. 2019).

Office Action for Japanese Application No. 2022-534842, dated Dec. 3, 2024, Japanese Patent Office, Tokyo, Japan, 9 pages.

Office Action for Russian Application No. 2022117235, dated Feb. 27, 2024, Federal Service for Intellectual Property, Moscow, Russia, 7 pages.

Ohnuki, Y., and Kurosawa, H., "Importance of the Structuration of Cells in the Differentiation Process of Human Induced Pluripotent Stem (hiPS) Cells: Effects of the Size of Embryoid Body on Cardiomyocyte Differentiation of hiPS cells," Clinical Times 2016(3):12-16, Kanto Publishing, Japan (2016).

Reubinoff, B.E., et al., "Embryonic Stem Cell Lines From Human Blastocysts: Somatic Differentiation in Vitro," Nature Biotechnology 18(4):399-404, Nature America Publishing, United States (Apr. 2000).

Saccone, S., et al., "The Highest Gene Concentrations in the Human Genome Are in Telomeric Bands of Metaphase Chromosomes," Proceedings of the National Academy of Sciences of the United States of America 89(11):4913-4917, National Academy of Sciences, United States (Jun. 1992).

Schopperle, W.M., and Dewolf, W.C., "The TRA-1-60 and TRA-1-81 Human Pluripotent Stem Cell Markers Are Expressed on Podocalyxin in Embryonal Carcinoma," Stem Cells 25(3):723-730, Oxford University Press, United Kingdom (Mar. 2007).

Thomson, J.A., et al., "Embryonic Stem Cell Lines Derived From Human Blastocysts," Science, 282(5391):1145-1147, American Association for the Advancement of Science, United States (Nov. 1998).

Wuchter, P., et al., "Evaluation of GMP-compliant Culture Media for in Vitro Expansion of Human Bone Marrow Mesenchymal Stromal Cells," Experimental Hematology 44(6):508-518, Elsevier Science Inc., Netherlands (Jun. 2016).

Zhonghua, W.J.Y., "Thoughts on Mesenchyma Stem Cell Transplantation for the Treatment of Novel Corona Virus Pneumonia," Chinese Critical Care Medicine 32(9):1139-1144, Editorial Department of Chinese Critical Care Medicine, Tianjin, China (2020).

International Search Report for International Application No. PCT/KR2020/017948. Korean Intellectual Property Office, Daejeon, mailed Mar. 22, 2021, 7 pages, with English Translation.

* cited by examiner

Method in related art(EB →ES-MSC)

Improved method (EB →ES-MSC)

METHOD FOR PREPARING MESENCHYMAL STEM CELLS FROM HUMAN PLURIPOTENT STEM CELLS AND MESENCHYMAL STEM CELLS PREPARED THEREBY

TECHNICAL FIELD

The present invention relates to a method for preparing mesenchymal stem cells from human pluripotent stem cells and, more particularly, to a method for preparing mesenchymal stem cells, wherein the mesenchymal stem cells exhibit increased safety and maintain their own characteristics for a long period of time even after a plurality of subcultures by utilizing a xeno-free and serum-free environment for preparing mesenchymal stem cells and spheroidal embryoid bodies to form mature embryoid bodies uniform in shape and size.

BACKGROUND ART

Stem cells are cells that can differentiate into various cells that constitute biological tissues, and collectively refer to undifferentiated cells in the pre-differentiation stage which can be obtained from each tissue of an embryo, a fetus and an adult. Stem cells differentiate into specific cells by a differentiation stimulus (environment), can reproduce (self-renewal) the same cells as themselves by cell division, and thus have properties of proliferation (expansion), unlike cells whose differentiation is completed and cell division is stopped, and are characterized by having plasticity in differentiation because stem cells can differentiate into different cells under different environments or by other differentiation stimuli.

Stem cells can be divided into pluripotent, multipotent, and unipotent stem cells according to their differentiation ability. Pluripotent stem cells are pluripotent cells with the potential to differentiate into all cells, and embryonic stem cells (ESCs), induced pluripotent stem cells (iPSCs) and the like correspond to pluripotent stem cells. Adult stem cells may be exemplified as pluripotent and/or unipotent stem cells.

Embryonic stem cells are formed from the inner cell mass of the blastocyst, which is the early stage of embryonic development, and have the potential to differentiate into all cells, so they can differentiate into any tissue cell. Embryonic stem cells are immortal, they can be cultured in an undifferentiated state, and they have traits that can be passed on to the next generation because they can prepare germ cells unlike adult stem cells (Thomson et al, *Science,* 282: 1145-1147, 1998; Reubinoff et al, *Nat Biotechnol,* 18: 399-404, 2000).

Human embryonic stem cells are prepared by isolating and culturing only the inner cell mass during the formation of human embryos, and currently, human embryonic stem cells made worldwide are obtained from frozen embryos left after in vitro fertilization treatment. Although various attempts have been made to use pluripotent human embryonic stem cells that can differentiate into all cells as a cell therapeutic agent, the risk of cancer and the high barrier of immune rejection are still not fully controlled.

Meanwhile, induced pluripotent stem cells (iPSCs), which are included in the concept of pluripotent stem cells, are cells in which adult cells that have been completely differentiated are dedifferentiated in various ways and returned to the state of pluripotent stem cells, which is the initial stage of differentiation. To date, it has been reported that dedifferentiated cells exhibit almost the same characteristics as embryonic stem cells, which are pluripotent stem cells, in gene expression and differentiation ability. However, even in the case of iPSCs, the risk of immune rejection can be excluded using autologous cells, but the risk of cancer still remains as a problem to be solved.

As an alternative to overcome this problem, mesenchymal stem cells having no risk of cancer along with immunomodulatory function have been proposed. It has been reported that mesenchymal stem cells are pluripotent cells capable of differentiating into adipocytes, osteocytes, chondrocytes, myocytes, nerve cells, and cardiomyocytes, and also have a function of regulating an immune response. Although mesenchymal stem cells can be isolated and cultured from various tissues, it is not easy to clearly define mesenchymal stem cells because the ability and cell surface markers for each origin are slightly different. However, when stem cells can differentiate into osteocytes, chondrocytes, and myocytes, have a spindle-shaped form, and express basic cell surface markers such as CD73(+), CD105 (+), CD34(−) and CD45(−), those stem cells are generally defined as mesenchymal stem cells.

In addition, in order for mesenchymal stem cells to be used as a cell therapeutic agent, the minimum number of cells (about $1\times10^9$) required in the field of regenerative medicine and/or cell therapy should be satisfied, and the required number of cells will be further increased when even experiments in which appropriate conditions are determined and criteria are determined are taken into consideration. Therefore, to supply this amount from existing mesenchymal stem cells of various origins, at least 10 passages are required in in vitro experiments, and in this case, cells are aged and modified, so mesenchymal stem cells may not be suitable for achieving the object as a cell therapeutic agent any more. After all, cells applied to clinical trials and cells undergoing quality evaluation are inevitably different, so there is a disadvantage in that a risk that occurs in the process of post-verification form cannot be excluded. Therefore, in order to use mesenchymal stem cells as a cell therapeutic agent, it is important to maintain the characteristics of mesenchymal stem cells without being modified even though a subculture is repeated for a long period of time.

As an alternative to these adult-derived mesenchymal stem cells, a method for inducing differentiation from human pluripotent stem cells to mesenchymal stem cells has been proposed. However, the methods known to date are expensive, and have disadvantages such as an induction process by specific cytokines (for example, BMP) that requires the control of concentration or the induction of xeno feeder cells having a risk of xeno pathogens, and the use of fetal bovine serum (FBS). The method for inducing differentiation from human pluripotent stem cells to mesenchymal stem cells in the related art (WO 2011052818) has a possibility of influx of foreign cells through the use of feeder cells because human pluripotent stem cells are cultured on xeno feeder cells, which may be a problem for xeno pathogens during the culture of human pluripotent stem cells. In addition, due to concerns about zoonotic infections caused by the use of animal-derived serum such as bovine serum or fetal calf serum during the culture of pluripotent stem cells, it is necessary to improve a xeno-free and serum-free culture method that does not use foreign animal serum when a cell therapeutic agent is developed in the future.

Thus, the present inventors have made intensive studies to solve the problems related to safety of stem cells and mass production of stem cells in order to commercialize mesenchymal stem cells differentiated from human pluripotent stem cells as a cell therapeutic agent, and as a result, confirmed that the cell safety was maximized through a xeno-free and serum-free environment, spheroidal embryoid bodies can be used to form mature embryoid bodies uniform in shape and size, and mesenchymal stem cells whose differentiation was induced therefrom maintained the characteristics of mesenchymal stem cells for a long period of time even after repeated subcultures, thereby completing the present invention.

DISCLOSURE

Technical Problem

An object of the present invention is to provide a method for preparing mesenchymal stem cells from human pluripotent stem cells available as a cell therapeutic agent by preparing mesenchymal stem cells, in which safety problem caused by contamination of foreign cell- and foreign animal-derived materials is solved and the characteristics of mesenchymal stem cells are maintained for a long period of time even after repeated subcultures.

Another object of the present invention is to provide mesenchymal stem cells prepared by the method and a cell therapeutic agent using the same.

Technical Solution

To achieve the objects, the present invention provides a method for preparing mesenchymal stem cells whose long-term subculture stability is maintained, from human pluripotent stem cells, the method comprising:

(a) culturing human pluripotent stem cells in a serum-free pluripotent stem cell culture medium without xeno feeder cells to obtain a colony of human pluripotent stem cells and isolating human pluripotent stem cells from the colony;

(b) forming single spheroidal embryoid bodies by suspending the isolated pluripotent stem cells in an embryoid body formation medium, and then culturing the isolated pluripotent stem cells such that pluripotent stem cells are aggregated;

(c) forming mature embryoid bodies by suspension-culturing the embryoid bodies in an embryoid body maturation medium;

(d) inducing differentiation into mesenchymal stem cells by adherently culturing the embryoid bodies in a xeno-free and serum-free mesenchymal stem cell culture medium; and (e) proliferating and culturing the differentiated mesenchymal stem cells in a xeno-free and serum-free mesenchymal stem cell culture medium while maintaining the identity of mesenchymal stem cells.

The present invention also provides mesenchymal stem cells differentiated and induced from human pluripotent stem cells prepared by the method and a cell therapeutic agent including the mesenchymal stem cells.

MODES OF THE INVENTION

Figure 1:
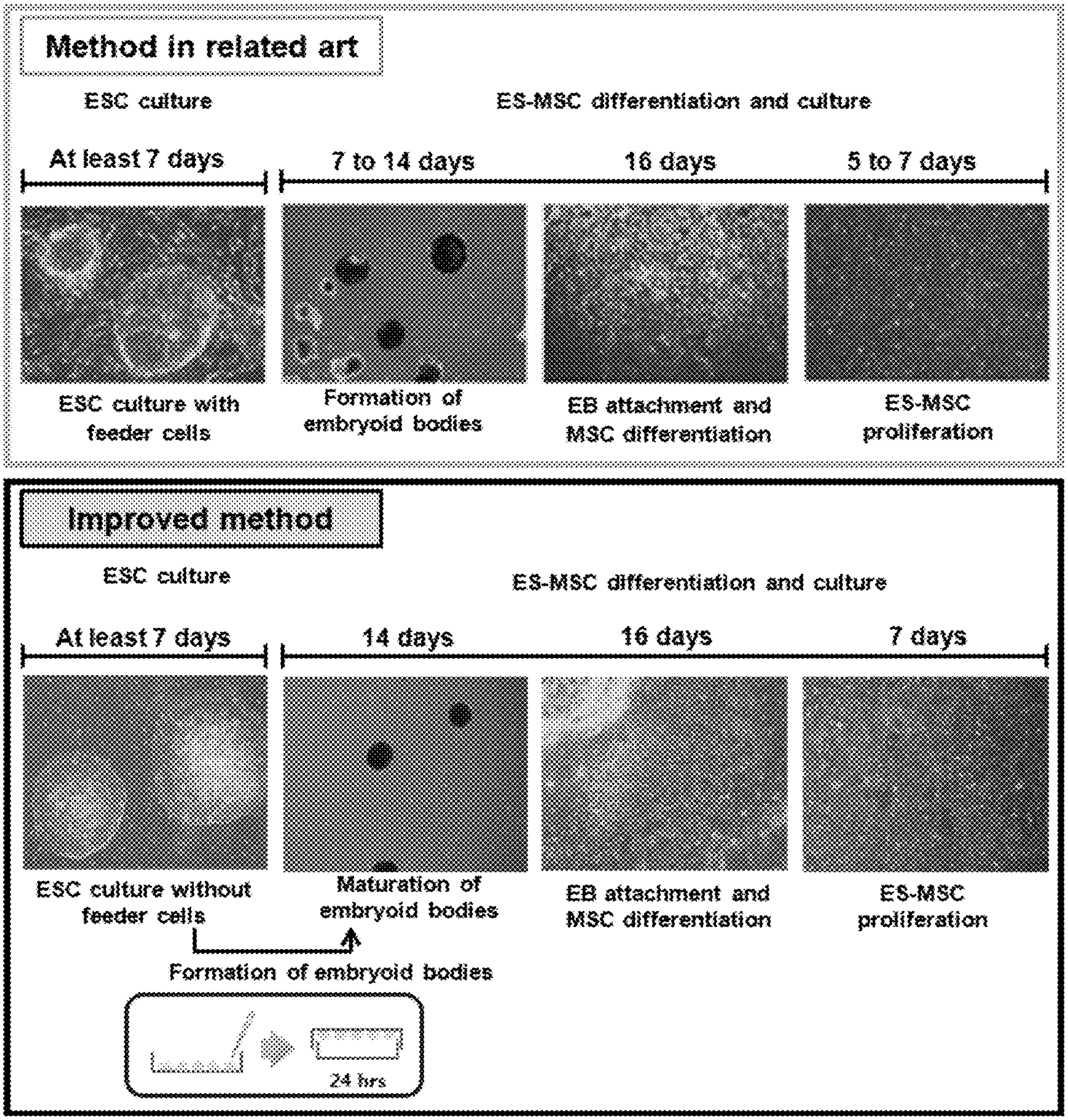
FIG. 1 is a schematic view of an existing method for preparing mesenchymal stem cells derived from pluripotent stem cells (WO 2011052818) and an improved method for preparing mesenchymal stem cells derived from pluripotent stem cells of the present invention.

Unless otherwise defined, all technical and scientific terms used herein have the same meaning as commonly understood by a person with ordinary skill in the art to which the present invention pertains. In general, the nomenclature used herein is well known and commonly used in the art.

As used herein, the term "stem cells" refers to master cells capable of being regenerated in a non-limiting manner to form specialized cells of tissues and organs. Stem cells are pluripotent or multipotent cells that can develop. Stem cells can divide into two daughter stem cells, or one daughter stem cell and one derived ('transit') cell, and then proliferate into cells in a mature and intact form of tissue. Such stem cells may be classified by various methods. One of the most commonly used methods is according to the differentiation ability of stem cells, and stem cells can be classified into pluripotent stem cells capable of differentiating into three germ layers, multipotent stem cells which are limited to differentiation into specific germ layers or higher, and unipotent stem cells capable of differentiating into specific germ layers only.

As used herein, the term "pluripotent stem cells" refers to stem cells having totipotency capable of differentiating into all three germ layers constituting a living body, and generally, embryonic stem cells (ESCs) and induced pluripotent stem cells (iPSCs) correspond thereto. Adult stem cells may be classified into multipotent or unipotent stem cells.

As used herein, the term "mesenchymal stem cells" refers to stem cells possessing multipotency capable of differentiating into cells such as adipocytes, osteocytes, chondrocytes, myocytes, nerve cells, and cardiomyocytes.

As used herein, the term "differentiation" refers to a phenomenon in which a cell's structure or function is specialized during cell division, proliferation and growth. Pluripotent mesenchymal stem cells differentiate into progenitor cells of limited lineage (for example, mesodermal cells) and then may further differentiate into other forms of progenitor cells (for example, osteoblasts, and the like), and then may differentiate into terminal differentiated cells (for example, adipocytes, osteocytes, chondrocytes, and the like) that play a characteristic role in specific tissues (for example, bone, and the like).

As used herein, the term "embryoid body (EB)" refers to an aggregate of pluripotent stem cells produced to induce the differentiation of pluripotent stem cells. In the present invention, the "mature embryoid body" is an aggregate of pluripotent stem cells, that is, an embryoid body at a state in which the embryoid body repeatedly divides through suspension culture and becomes larger in size, and the mature embryoid body in the present invention is used as a material for inducing differentiation into mesenchymal stem cells.

As used herein, the term "cell therapeutic agent" refers to a drug used for the purpose of treatment, diagnosis, and prevention, by using a cell or tissue prepared through isolation from a human, culture and specific manipulation (US FDA regulations), and specifically, it refers to a drug used for the purpose of treatment, diagnosis, and prevention through a series of actions of in vitro multiplying and sorting living autologous, allogenic and xenogenic cells or changing the biological characteristics of cells by other methods for the purpose of recovering the functions of cells or tissues. Cell therapeutic agents are broadly classified into somatic cell therapeutic agents and stem cell therapeutic agents according to the degree of cell differentiation, and the present invention particularly relates to a stem cell therapeutic agent.

In the present invention, to solve the problems related to cell safety and mass production in order to commercialize the mesenchymal stem cells induced to differentiate from human pluripotent stem cells as a cell therapeutic agent, human pluripotent stem cells were induced to differentiate into mesenchymal stem cells in a feeder cell-free, xeno-free, and serum-free environment. In addition, a single spheroidal embryoid body was allowed to be formed by intercellular aggregation of human pluripotent stem cells, the quality difference between mature embryoid bodies was minimized by suspension-culturing such embryoid bodies to form mature embryoid bodies uniform in shape and size, and the resulting efficiency and consistency of differentiation into mesenchymal stem cells were improved. The mesenchymal stem cells thus prepared showed an exceptional effect in which the mesenchymal stem cell characteristics were stably maintained even after repeated long-term subcultures of 20 or more passages. That is, the present invention provides human pluripotent stem cell-derived mesenchymal stem cells which are safe without contamination with a foreign cell and a foreign animal-derived material, have uniform quality through the formation of mature embryoid bodies uniform in shape and size using spheroidal embryoid bodies, and can be mass produced because the stability of subculture is excellent for a long period of time. Therefore, the mesenchymal stem cells with enhanced productivity and safety prepared by the method of the present invention make it possible to continuously supply a large amount of mesenchymal stem cells required in the fields of regenerative medicine and cell therapy.

Therefore, in an aspect, the present invention relates to a method for preparing mesenchymal stem cells from human pluripotent stem cells, the method comprising:

(a) culturing human pluripotent stem cells in a serum-free pluripotent stem cell culture medium without xeno feeder cells to obtain a colony of human pluripotent stem cells and isolating human pluripotent stem cells from the colony;

(b) forming single spheroidal embryoid bodies by suspending the isolated pluripotent stem cells in an embryoid body formation medium, and then culturing the isolated pluripotent stem cells such that pluripotent stem cells are aggregated;

(c) forming mature embryoid bodies by suspension-culturing embryoid bodies in an embryoid body maturation medium;

(d) inducing differentiation into mesenchymal stem cells by adherently culturing the embryoid bodies in a xeno-free and serum-free mesenchymal stem cell culture medium; and (e) proliferating and culturing the differentiated mesenchymal stem cells in a xeno-free and serum-free mesenchymal stem cell culture medium while maintaining the identity of mesenchymal stem cells.

Hereinafter, each step of the method will be described in detail.

(a) culturing human pluripotent stem cells in serum-free pluripotent stem cell culture medium without xeno feeder cell to obtain colony of human pluripotent stem cells and isolating human pluripotent stem cells from the colony In the present invention, the human pluripotent stem cells may be embryonic stem cells or induced pluripotent stem cells. The human pluripotent stem cells are in an undifferentiated state.

In general, a support is required to maintain an undifferentiated state in culturing human pluripotent stem cells in the related art, and as a human pluripotent stem cell support in the related art, murine embryo-derived fibroblasts have been preferentially used. However, since the influx of various pathogens between different species is recognized as a problem when trying to use pluripotent stem cells clinically, the potential as a support for various human-derived cells has been reported as an alternative to the problem. However, it is impossible to overcome disadvantages in that it is also impossible to completely exclude heterologous pathogens, foreign factors (for example, bFGF, IGF, ACTIVIN, and the like) are essential for maintaining an undifferentiated state, and it is impossible to continuously supply the human-derived cells for long-term culture, and the like.

However, in the method of the present invention, an undifferentiated state can be maintained even when a culture vessel coated with vitronectin is used without xeno feeder cells, and human pluripotent stem cells are cultured in a serum-free medium.

In the present invention, the pluripotent stem cells in Step (a) are preferably cells cultured in a culture vessel coated with a human-derived extracellular matrix, an extracellular matrix that does not contain animal-derived components, or a synthetic material capable of replacing the extracellular matrix, but are not limited thereto.

The human-derived extracellular matrix is preferably vitronectin, collagen, or laminin, and the extracellular matrix that does not contain an animal-derived component other than human is preferably an animal component-free Matrigel, and the synthetic material capable of replacing the extracellular matrix is preferably heparan sulfate proteoglycan, but they are not limited thereto.

That is, the method of the present invention may be characterized in that it is performed in a medium free of xeno feeder cells, cytokines and xenogeneic materials in all steps. That is, the method of the present invention may be characterized in that it is performed in a feeder cell-free, xeno-free and serum-free environment.

In particular, in the method in the related art (WO 2011052818), pluripotent stem cells were cultured using xeno feeder cells cultured in a medium containing FBS, but the present invention may be characterized by using human pluripotent stem cells cultured in a serum-free medium without xeno feeder cells.

In addition, in the related art, DMEM/F12 containing KSR, NEAA, β-mercaptoethanol, and bFGF was used as a pluripotent stem cell culture medium, but in the present invention, a serum-free pluripotent stem cell culture medium is used. In the present invention, the serum-free medium for culturing the human pluripotent stem cells in Step (a) may be TeSR-Essential 8 (TeSR-E8) medium, TeSR-2 medium or StemMACS iPS-Brew XF, human medium, but is not limited thereto.

(b) forming single spheroidal embryoid bodies by suspending isolated pluripotent stem cells in embryoid body formation medium, and then culturing isolated pluripotent stem cells such that pluripotent stem cells are aggregated;

In the present invention, it is characterized in that mature embryoid bodies uniform in shape and size are used to induce differentiation from human pluripotent stem cells to mesenchymal stem cells. In the method in the related art, it was difficult to expect consistent differentiation efficiency into mesenchymal stem cells because it was not possible to produce embryoid bodies uniform in shape and size, but in the present invention, these technical limitations were overcome by allowing a single spheroidal form of human pluripotent stem cells to be formed by intercellular aggregation and suspension-culturing these embryoid bodies to form mature embryoid bodies uniform in shape and size. Through this, exceptionally excellent mesenchymal stem cells, which improved the differentiation efficiency of human pluripotent stem cell-derived mesenchymal stem cells and maintained stem cell characteristics for a long time of time even after repeated subcultures, were prepared.

In the method in the related art (WO 2011052818), pluripotent stem cells were suspension-cultured during embryoid body formation, but in the present invention, in order that the pluripotent stem cells aggregate with each other to form a single spheroidal embryoid body, pluripotent stem cells were inoculated onto a lid of a culture vessel and then the culture vessel was inverted upside down to perform hanging drop culture for 24 hours such that the cells could aggregate by gravity, and the thus-formed cell aggregates, that is, embryoid bodies were suspension-cultured and matured into mature embryoid bodies. As a result, as illustrated in FIG. 1, mature embryoid bodies uniform in shape and size were formed, and these mature embryoid bodies can exhibit consistent differentiation efficiency into mesenchymal stem cells and stability during subculture.

Figure 4:
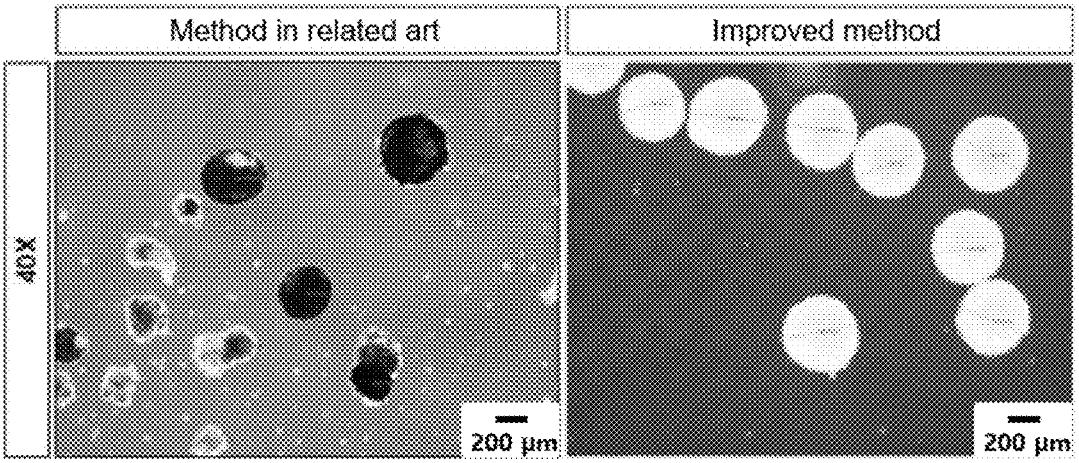
FIG. 4 illustrates photographs showing the sizes and morphologies of the embryoid bodies prepared by the existing preparation method (WO 2011052818) and the embryoid bodies prepared by the improved method of the present invention.
Figure 5:
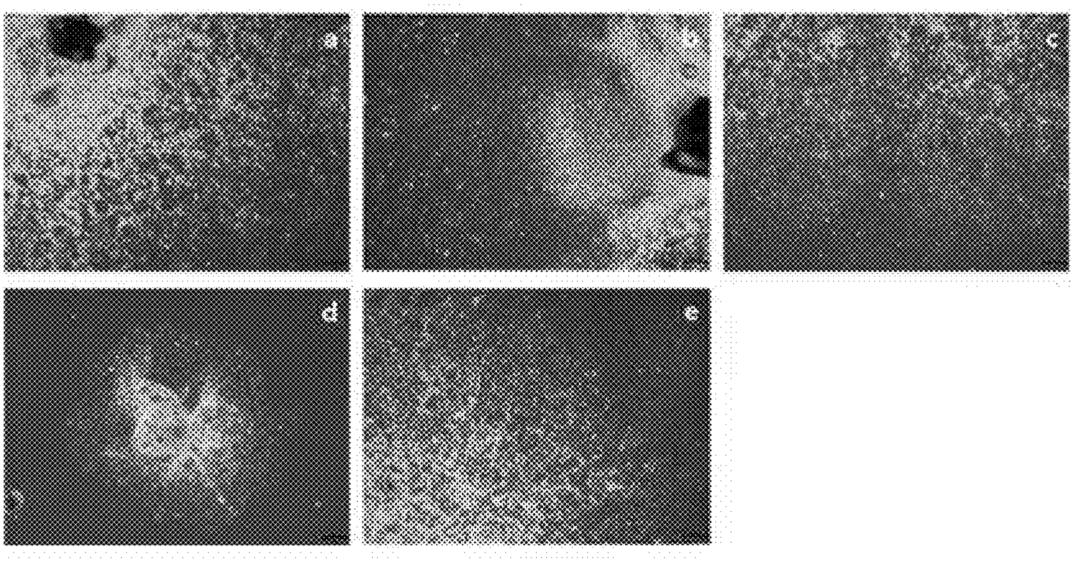
FIG. 5 illustrates photographs showing the efficiencies of differentiation from the embryoid bodies prepared by the existing preparation method (WO 2011052818) and the embryoid bodies prepared by the improved method of the present invention into mesenchymal stem cells and the cell morphologies.
Figure 5:
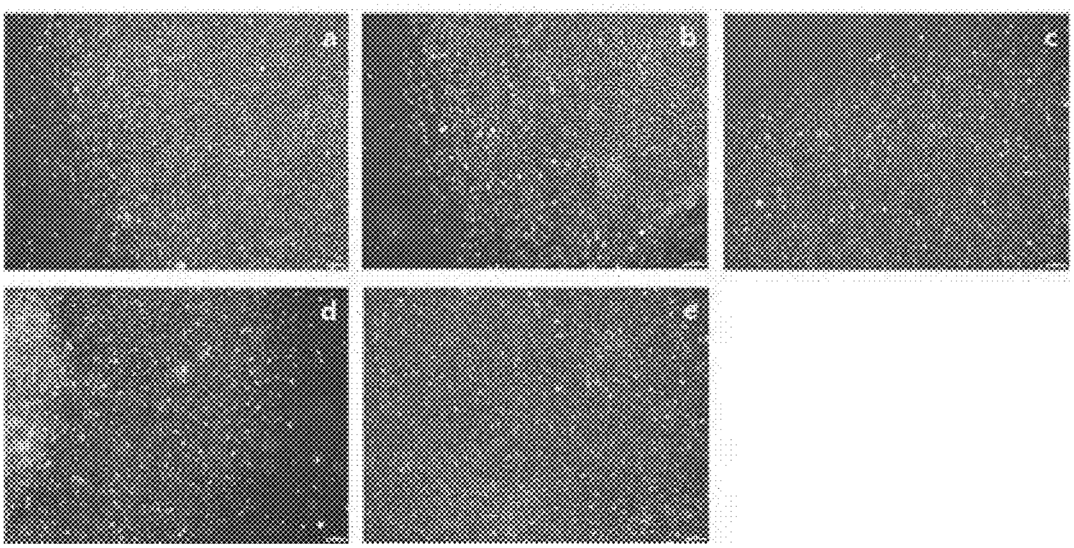

FIG. 4 shows that the size and shape of the mature embryoid body prepared by the method in the related art are not uniform, whereas the mature embryoid body prepared by the method of the present invention has a uniform size of 300 to 500 and the shape is also constant as a spheroid. In addition, it can be seen that the mesenchymal stem cells differentiation-induced from the mature embryoid body thus prepared have a constant differentiation efficiency and a constant size of the mesenchymal stem cells. However, the mesenchymal stem cells differentiation-induced from the embryoid body prepared by the method in the related art are not uniform in differentiation efficiency as well as in cell shape (FIG. 5).

Moreover, the mesenchymal stem cells differentiation-induced from mature embryoid bodies uniform in shape and size surprisingly showed 90% or more expression of the mesenchymal stem cell surface markers CD29, CD44, CD73, and CD105 by passage 20. In addition, the expression of cell surface markers for a hematopoietic stem cell-specific surface marker CD45, an MHC class type II marker HLA-DR, and pluripotent stem cell-specific surface markers SSEA-3, TRA-1-60, and TRA-1-81 was found to be 2% or less. That is, since the mesenchymal stem cells prepared by the method of the present invention can be subcultured for a long period of time and maintain high purity, it is possible to mass-produce stem cells that can be used as a cell therapeutic agent. When the mesenchymal stem cells prepared by the method in the related art meet the criteria for use as a cell therapeutic agent, the cells are aged and modified and thus are no longer suitable for achieving the purpose as a cell therapeutic agent. In the end, there was a disadvantage in that cells applied to clinical trials and cells undergoing quality evaluation had to be different. However, since the mesenchymal stem cells of the present invention are not modified even after repeated subcultures for a long period of time for use as a cell therapeutic agent and maintain the quality characteristics of the mesenchymal stem cells, the mesenchymal stem cells of the present invention are very useful for commercializing a cell therapeutic agent.

Although a method for controlling the size of an embryoid body (KR 10-2013-0013537) or a method for forming embryoid bodies uniform in size through a hanging drop method (KR 10-2007-0075006), and the like are known, it is known that the formation of embryoid bodies uniform in size affects cell differentiation efficiency, but the effect on the inhibition of senescence or cell modification of mesenchymal stem cells differentiation-induced from embryoid bodies uniform in size is not known at all. However, in the present invention, it was confirmed that mature embryoid bodies uniform in shape and size were formed to maintain the mesenchymal stem cell characteristics of the mesenchymal stem cells differentiation-induced therefrom for a long period of time until passage 20. In particular, it was confirmed that in the mesenchymal stem cells differentiation-induced from embryoid bodies prepared by the method in the related art, the expression of CD105 was reduced by 43.6% at passage 6 and by 26.6% at passage 12 (Table 2). That is, the stem cells prepared by the method in the related art do not maintain the characteristics of mesenchymal stem cells until passage 20, but the stem cells of the present invention can maintain the characteristics of mesenchymal stem cells for a long period of time until passage 20 through the formation of embryoid bodies uniform in size.

Therefore, the present invention prepared mesenchymal stem cells which are highly safe by employing a feeder cell-free, xeno-free, and serum-free culture environment to solve the problem of contamination with a foreign animal-derived material, and simultaneously prepared human pluripotent stem cell-derived mesenchymal stem cells having exceptional effects of improving the differentiation efficiency to mesenchymal stem cells by utilizing spheroidal embryoid bodies to form mature embryoid bodies uniform in shape and size and stably maintaining mesenchymal stem cell characteristics even after long-term subcultures, such as 20 or more passages.

As used herein, the “spheroidal embryoid body” refers to a round spherical cell aggregate, wherein the spheroidal form is often expressed as a spheroid form.

In the present invention, any culture method capable of inducing intercellular aggregation of pluripotent stem cells can be used for the embryoid body in Step (b). Any culture method capable of preparing an aggregate of pluripotent stem cells, that is, a single spheroidal embryoid body is possible and not limited. For example, the embryoid body in Step (b) may be formed by hanging drop culture, or culture using a V-shape tube, a round shape 96 well plate, or a conical tube.

In the present invention, any medium capable of inducing cell aggregation between pluripotent stem cells can be used as the embryoid body formation medium in Step (b). For example, the embryoid body formation medium in Step (b) may be an Aggrewell EB formation medium, Gibco Essential 6 Medium, CTS Essential 6 Medium, or TeSR-E6. The culture in Step (b) may be performed for 18 hours to 30 hours, for example, 20 hours to 28 hours, 22 hours to 26 hours, such as 24 hours.

(c) forming mature embryoid bodies by suspension-culturing embryoid bodies in embryoid body maturation medium;

Step (c) is a step in which the embryoid body is grown while being suspension-cultured, and the mature embryoid body obtained in this step is characterized by having a uniform shape and size.

The fact that mature embryoid bodies have “uniform shape and size” means that mature embryoid bodies obtained by suspension-culturing spheroidal embryoid bodies are uniform in shape and size. The shape of the mature embryoid bodies is spheroidal like the embryoid body, and the size of the mature embryoid body is uniform within ±15% of the average size of all mature embryoid bodies. That is, assuming that the average size of the mature embryoid bodies is 100%, the minimum size of the mature embryoid body is within 90% and the maximum size of the mature embryoid body is within 120%, and the size thereof is quite uniform. Preferably, the size of the mature embryoid body is uniform with a size of ±10% of the average size of all mature embryoid bodies. In this case, assuming that the average size of the mature embryoid bodies is 100%, the minimum size of the mature embryoid body is 90%, and the maximum size of the mature embryoid body is within 110%. Although the average size of the mature embryoid bodies may vary depending on the maturation culture conditions and period of the embryoid body, the average size of the mature embryoid bodies suitable for induction of differentiation into stem cells may be 350 to 450 μm, for example, 380 to 420 μm. Preferably, the mature embryoid body has a uniform size of 300 to 500 μm.

In the present invention, the suspension culture in Step (c) is performed using an embryoid body maturation medium for embryoid body maturation. A generally known embryoid body maturation medium may be used, and is not particularly limited. Although not limited thereto, in an exemplary embodiment of the present invention, the embryoid body maturation medium in Step (c) may be a basic medium supplemented with knock out serum replacement (KSR), non-essential amino acids (NEAA) and β-mercaptoethanol. The basic medium may be DMEM/F12, alpha MEM, Ham’s F12 media, or DMEM, but is not limited thereto.

The suspension culture in Step (c) may be performed for 10 to 18 days, for example, 12 to 16 days, such as, 14 days, but is not limited thereto.

(d) inducing differentiation into mesenchymal stem cells by adherently culturing embryoid bodies in xeno-free and serum-free mesenchymal stem cell culture medium In the case of inducing differentiation from human pluripotent stem cells to mesenchymal stem cells, the induction of differentiation is generally initiated by adding a cytokine, for example, bone morphogenetic protein (BMP), and the like, from the outside, but in the present invention, it was confirmed that differentiation into mesenchymal stem cells was naturally induced without the addition of BMP and the like. In the method in the related art (WO 2011052818), a DMEM medium containing FBS was used for differentiation of mesenchymal stem cells, and an EGM2-MV medium containing FBS was also used for proliferation culture. However, in the present invention, proliferation and culture of mesenchymal stem cells were performed in a xeno-free and serum-free environment.

In the present invention, the mesenchymal stem cell culture medium used in Step (d) may be a xeno-free and serum-free medium containing L-glutamine. The total concentration of L-glutamine in the medium is preferably used in accordance with 2 to 4 mM, but is not limited thereto.

Examples of the xeno-free and serum-free mesenchymal stem cell culture medium in Step (d) include a Stempro SFM xeno-free medium, a PRIME-XV MSC expansion XSFM medium, a Human Mesenchymal-XF Expansion medium, an MSC Nutristem XF medium, a StemMACS MSC expansion media kit XF, human medium, or a medium containing 5 to 20% human platelet lysate instead of FBS, but are not limited thereto.

Further, in the present invention, the induction of differentiation into mesenchymal stem cells in Step (d) may be 12 to 20 days, for example, 14 to 18 days, such as 16 days, but is not limited thereto.

In an exemplary embodiment of the present invention, differentiation of mesenchymal stem cells was induced in a Stempro MSC SFM Xeno-free medium that does not contain differentiation inducing factors and serum.

(e) proliferating and culturing the differentiated mesenchymal stem cells in xeno-free and serum-free mesenchymal stem cell culture medium while maintaining identity of mesenchymal stem cells Step (e) is a step of proliferating and culturing differentiation-induced mesenchymal stem cells. In order to commercialize a cell therapeutic agent containing human mesenchymal stem cells, it is a very important issue whether the mesenchymal stem cells obtained in this step are secured in a sufficient amount, while simultaneously maintaining the identity of the mesenchymal stem cells, that is, the characteristics as mesenchymal stem cells.

In the present invention, in the proliferation culture of the differentiation-induced mesenchymal stem cells, the mesenchymal stem cells are cultured in a xeno-free medium to which additional differentiation inducing factors and fetal bovine serum (FBS) are not added.

As in Step (d), in the present invention, the mesenchymal stem cell culture medium used in Step (e) may be a xeno-free and serum-free medium containing L-glutamine. The total concentration of L-glutamine in the medium is preferably used in accordance with 2 to 4 mM, but is not limited thereto.

Examples of the xeno-free and serum-free mesenchymal stem cell culture medium in Step (e) include a Stempro SFM xeno-free medium, a PRIME-XV MSC expansion XSFM medium, a Human Mesenchymal-XF Expansion medium, an MSC Nutristem XF medium, a StemMACS MSC expansion media kit XF, human medium, or a medium containing 5 to 20% human platelet lysate instead of FBS, but are not limited thereto.

In an exemplary embodiment of the present invention, a Stempro MSC SFM medium to which FBS was not added was used as a mesenchymal stem cell proliferation medium, but the present invention is not limited thereto, and a medium that does not contain a heterologous material such as a heterologous protein (xeno-free) may be used.

As described above, in order to use mesenchymal stem cells as a cell therapeutic agent, it is necessary to first supply a sufficient amount of cells, and for this purpose, the subculture of mesenchymal stem cells is required. However, when the subculture is continued, there is a problem in that the mesenchymal stem cells age and lose their division ability and lose their activity (differentiation ability). In this regard, in the present invention, it was confirmed that the characteristics and activity of the mesenchymal stem cells could be maintained for 20 or more passages during ex vivo culture even in a xeno-free and serum-free medium (Table 1). That is, the mesenchymal stem cells prepared by the method of the present invention can maintain the characteristics of the mesenchymal stem cells for a long period of time, and thus can be used as a cell therapeutic agent through mass production. These characteristics may be achieved through a xeno-free and serum-free mesenchymal stem cell preparation environment and the preparation of embryoid bodies uniform in size.

Mesenchymal stem cells are defined by a uniform spindle-shaped fingerprint pattern and the expression levels of basic cell surface markers such as CD73(+), CD105(+), CD34(−), and CD45(−), and can be differentiated into osteocytes, chondrocytes, adipocytes, and the like.

In the present invention, the mesenchymal stem cells in Step (e) may be characterized by being mesenchymal stem cells possessing multipotency capable of differentiating into cells selected from the group consisting of adipocytes, osteocytes, chondrocytes, myocytes, nerve cells and cardiomyocytes.

In an exemplary embodiment of the present invention, in order to confirm the stem cell characteristic persistence (consistency) according to the subculture of pluripotent stem cell-derived mesenchymal stem cells, a change in cell surface markers up to passage 20 was comparatively analyzed. As a result of comparatively analyzing the expression of cell surface marker for mesenchymal stem cell surface markers CD29, CD44, CD73, and CD105, a hematopoietic stem cell-specific surface marker CD45, an MEW class type II marker HLA-DR, and pluripotent stem cell-specific surface markers SSEA-3, TRA-1-60 and TRA-1-81 from passage 12 to passage 20, it was confirmed that the expression of mesenchymal stem cell surface markers CD29, CD44, CD73, and CD105 was maintained at 90% or more until passage 20 (Table 1). Furthermore, in the pluripotent stem cell-derived mesenchymal stem cells prepared by the method in the related art (WO 2011052818), the expression of CD105 was shown to be less than 50% in passage 6 cells, and in particular, it was confirmed that the expression was reduced to 26.6% after passage 12 (Table 2). That is, the stem cells prepared by the method in the related art do not maintain the characteristics of mesenchymal stem cells until passage 20, but the stem cells of the present invention can maintain the characteristics of mesenchymal stem cells for a long time up to passage 20 through the formation of a mature embryoid body having a uniform shape and size.

CD105 is known as one of the specific surface markers of mesenchymal stem cells, and according to a report by Duff SE et al. in 2003, it was reported that CD105 plays an important role in vascular regeneration by mesenchymal stem cells (*The FASEB Journal* 2003; 17(9):984-992). In addition, CD105 is reduced after not only differentiation of mesenchymal stem cells into osteocytes (Levi B et al., *The Journal of Biological Chemistry.* 2011; 286(45): 39497-39509), but also differentiation of mesenchymal stem cells into cells such as osteocytes, chondrocytes, and adipocytes, and thus is known to play an important role in maintaining the stemness of mesenchymal stem cells (Jin H J et al., *BBRC* 2009;381(4):676-681).

In the present invention, the mesenchymal stem cells in Step (e) may be characterized by being mesenchymal stem cells expressing CD29(+), CD44(+), CD73(+) and CD105 (+) cell surface markers.

In the present invention, the expression of the cell surface marker is preferably maintained at 90% or more in mesenchymal stem cells of 20 or more passages, more preferably, the expression of a CD105(+) cell surface marker in mesenchymal stem cells of 20 or more passages is maintained at 90% or more, but is not limited thereto.

In the present invention, the mesenchymal stem cells in Step (e) may be characterized by being mesenchymal stem cells of CD34(−), CD45(−), HLA-DR(−), TRA-1-60(−), and TRA-1-81(−).

In another aspect, the present invention relates to mesenchymal stem cells differentiated from human pluripotent stem cells prepared by the method.

The differentiation-induced mesenchymal stem cells from human pluripotent stem cells prepared by the method of the present invention yielded the same results despite differences in race of origin (Asian and Western) and type (embryonic stem cells and induced pluripotent stem cells). The present invention provides a normalized differentiation induction and proliferation culture method that can be generally used to produce mesenchymal stem cells from human pluripotent stem cells having various genetic origins. That is, the prescribed method of the present invention is a method that can be generally used to induce differentiation of mesenchymal stem cells from pluripotent stem cells having various genetic backgrounds and/or culture environments.

In an exemplary embodiment of the present invention, mesenchymal stem cells were produced using SNUhES35/hES12011003 embryonic stem cells registered with the Stem Cell Bank in the National Center for Stem Cell Regenerative Medicine as human pluripotent stem cells, but the present invention is not limited thereto.

In addition, in another exemplary embodiment of the present invention, mesenchymal stem cells were produced using ESI-017/hES22014005 and ESI-035/hES22014006 registered with the Stem Cell Bank in the National Center for Stem Cell Regenerative Medicine as Western embryonic stem cells, but the present invention is not limited thereto, and embryonic stem cells such as ESI-049/hES22014007, ESI-051/hES22014008, and ESI-053/hES22014009 may be used.

In still another exemplary embodiment of the present invention, mesenchymal stem cells were produced using Asian induced pluripotent stem cells, but the present invention is not limited thereto.

In still another aspect, the present invention relates to a cell therapeutic agent comprising mesenchymal stem cells differentiation-induced from human pluripotent stem cells prepared by the method as an active ingredient. The cell therapeutic agent may comprises water for injection in addition to mesenchymal stem cells. In addition, the cell therapeutic agent may comprises a cryo-excipient used for freezing. The cryo-excipient is preferably CryoStor 10 (CS10) or STEM-CELLBANKER DMSO Free GMP grade that does not contain animal-derived components, but is not limited thereto. Typically, a cell therapeutic agent containing mesenchymal stem cells is administered to a subject at a dose of $1\times10^6$ to $1\times10^8$ cells/kg. The cell therapeutic agent comprising mesenchymal stem cells according to the present invention can be used without limitation for the treatment of various diseases, which are generally known as an effect of transplantation treatment of mesenchymal stem cells. In particular, the cell therapeutic agent comprising mesenchymal stem cells according to the present invention can be used to treat patients infected with the COVID-19 virus, severe acute pancreatitis (SAP), or the like.

EXAMPLES

Hereinafter, the present invention will be described in more detail through Examples. These Examples are only for exemplifying the present invention, and it will be apparent to those of ordinary skill in the art that the scope of the present invention is not interpreted to be limited by these Examples.

Example 1

Figure 2:
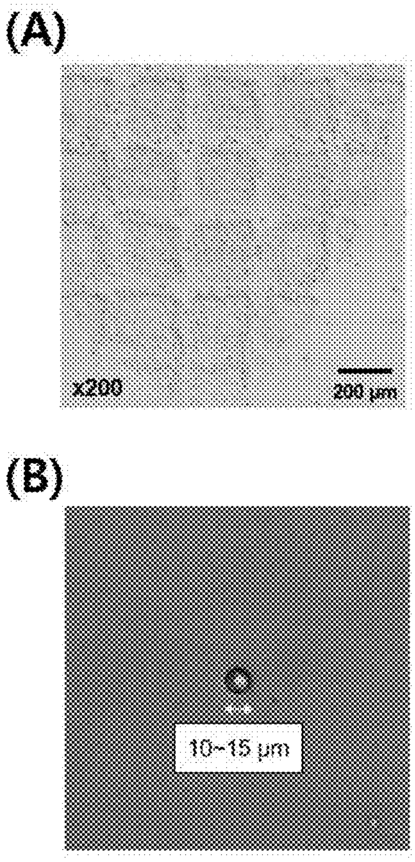
FIG. 2 shows photographs of a colony of human pluripotent stem cells obtained by culturing human pluripotent stem cells in a serum-free pluripotent stem cell culture medium without xeno feeder cells, and uniformly fragmenting them to a size of 200 μm×200 μm (FIG. 2A) and cell morphology isolated therefrom (FIG. 2B)

Method of Preparing Mesenchymal Stem Cells From Human Pluripotent Stem Cells 1-1: Confirmation of Culture and Pluripotency of Pluripotent Stem Cells in Feeder Cell Free, Xeno-Free and Serum-Free Environment In order to confirm whether pluripotent stem cells could be cultured in vitro while maintaining pluripotency in a feeder cell-free, xeno-free, and serum-free environment, a tissue culture vessel was coated with human vitronectin, which is a component of human extracellular matrix, to have a final concentration of 10 μg/mL, and then colonies of pluripotent stem cells were obtained by culturing undifferentiated human pluripotent stem cells (Korean-derived embryonic stem cells: SNUhES35/hES12011003) using a TeSR-2 or TeSR-Essential 8 (TeSR-E8) medium which is a xeno-free and serum-free medium (FIG. 1, an ESC culture photograph on the left side). When the confluency was 60% (20 or more colonies), the pluripotent stem cell colonies are uniformly fragmented into a size of about 200 μm×200 μm using the EZPassage Passaging Tool (FIG. 2A) and transferred to a conical tube using a pipette, the cells were settled by allowing the conical tube to stand, and then the supernatant was removed. The isolated pluripotent stem cells were confirmed as spherical cells having a size (diameter) of about 10 to 15 μm (FIG. 2B).

In order to confirm the pluripotency of pluripotent stem cells cultured in a feeder cell-free, xeno-free, and serum-free environment, the expression of OCT-4 and SSEA-4, which are pluripotency markers of stem cells, was confirmed through immunofluorescence staining.

Figure 3:
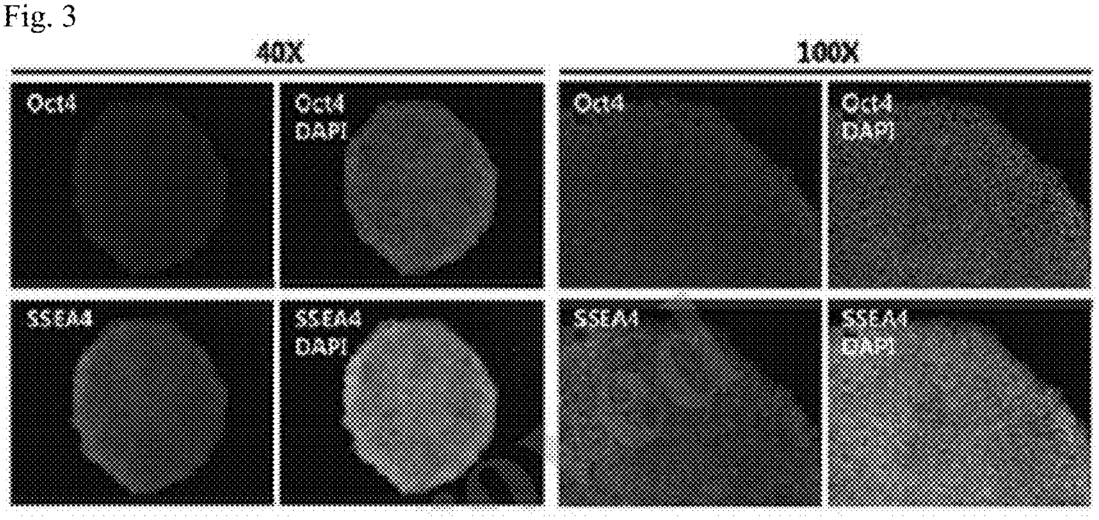
FIG. 3 illustrates the results of performing immunofluorescence staining on pluripotency markers OCT-4 and SSEA-4 in order to analyze the characteristics of pluripotent stem cells cultured in a feeder cell-free, xeno-free, and serum-free culture environment.

As a result, OCT-4 and SSEA-4, which are markers indicating pluripotency in pluripotent stem cells, cultured in a cell-free, xeno-free, and serum-free environment, were expressed. That is, it could be confirmed that the cultured pluripotent stem cells maintained pluripotency in a feeder cell-free, xeno-free, and serum-free environment (FIG. 3).

1-2: Formation of Mature Embryoid Body of Pluripotent Stem Cells

A certain volume of an embryoid body formation medium (Aggrewell EB Formation Medium) in which pluripotent stem cells were suspended was inoculated onto a lid of a Petri dish, and then hanging drop-cultured to form cell aggregates, that is, embryoid bodies. The embryoid bodies were again inoculated into an embryoid body maturation medium and then suspension-cultured to form a mature embryoid body having a certain size.

Specifically, an embryoid body formation medium (Aggrewell EB Formation Medium) (concentration of 400 μl per 20 colonies of human pluripotent stem cells) was put into a conical tube containing the isolated pluripotent stem cells for suspension, such that the isolated pluripotent stem cells became single cells in the embryoid body formation medium by pipetting. After 20 μl of the embryoid body formation medium in which the pluripotent stem cells were suspended was inoculated onto a lid of a tissue culture vessel, the tissue culture vessel was inverted upside down to perform hanging drop culture in an incubator at 37° C. and 5% $CO_2$ for 24 hours, such that the cells could be aggregated by gravity. After 24 hours of incubation, a single spheroidal form of cell aggregates, that is, embryoid bodies, were formed.

The formed embryoid bodies were suspension-cultured in a Petri dish using an embryoid maturation medium (DMEM/F12, 20% Knock out serum replacement (KSR), 0.1 mM non-essential amino acids (NEAA), 0.1 mM β-mercaptoethanol), and cultured for 14 days while exchanging the medium at intervals of 2 to 3 days (see FIG. 1).

As a result, it could be confirmed that mature embryoid bodies having a constant shape and a uniform size of 300 to 500 μm were formed as a spheroidal body (FIG. 4, a photograph of the improved method on the right side).

1-3: Induction and Proliferation of Mature Embryoid Bodies Into Mesenchymal Stem Cells Mature embryoid bodies cultured for 14 days were attached to a 6-well plate coated with a xeno-free substrate, CellStart™ (Thermo Fisher Scientific) (a concentration of 78 $\mu L/cm^2$). At the time of attachment, after 4 to 5 embryoid bodies were inoculated into each well, differentiation was induced using StemPro MSC SFM XenoFree™ (Thermo Fisher Scientific) which is a xeno-free and serum-free mesenchymal stem cell culture medium in order to induce differentiation into mesenchymal stem cells.

For induction of differentiation into mesenchymal stem cells and initial culture, culture was performed for 16 days without subculture while newly exchanging the medium once every 2 to 3 days.

After it was confirmed that the mesenchymal stem cells differentiated from the attached mature embryoid bodies sufficiently proliferated through a microscope, subculture was performed.

In addition, the pluripotent stem cell-derived mesenchymal stem cells thus prepared were subcultured, and cultured in an incubator at 37° C. and 5% $CO^2$ using a StemPro MSC SFM XenoFree medium for differentiation and proliferation in a xeno-free and serum-free environment.

FIG. 5 compares the efficiencies of differentiation from the embryoid bodies prepared by the existing preparation method (WO 2011052818) and the embryoid bodies prepared by the improved method of the present invention into mesenchymal stem cells and the cell morphologies. According to the method of the present invention, it could be confirmed that the differentiation efficiency into mesenchymal stem cells and the cell morphologies were constant due to the uniform shape and size of the embryoid body (bottom of FIG. 5). However, the mesenchymal stem cells differentiation-induced from the embryoid body prepared by the method in the related art are not uniform in differentiation efficiency as well as in cell morphologies (top of FIG. 5).

Example 2

Characterization of Pluripotent Stem Cell-Derived Mesenchymal Stem Cells 2-1. Analysis of Cell Surface Marker Expression in Mesenchymal Stem Cells In order to confirm whether the pluripotent stem cell-derived mesenchymal stem cells prepared by the method of Example 1 have the characteristics of mesenchymal stem cells, cell surface markers were analyzed using flow cytometry and it was analyzed whether the mesenchymal stem cells could differentiate into osteocytes, chondrocytes, and adipocytes.

Figure 6:
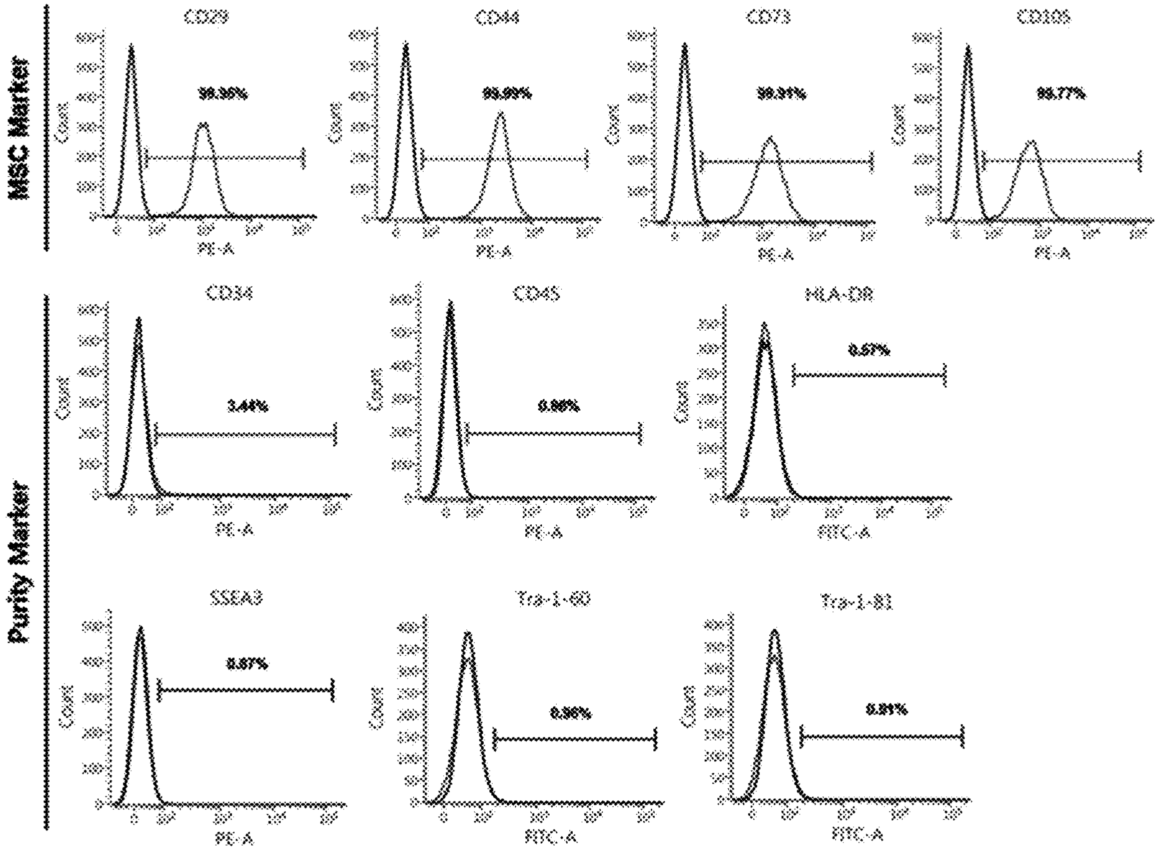
FIG. 6 illustrates the results of analyzing the cell surface marker expression of pluripotent stem cell-derived mesenchymal stem cells cultured in a feeder cell-free, xeno-free, and serum-free culture environment.

FIG. 6 illustrates the results of analyzing the cell surface marker expression of pluripotent stem cell-derived mesenchymal stem cells cultured in a feeder cell-free, xeno-free, and serum-free culture environment.

As a result, it was confirmed that CD73 and CD105, which are mesenchymal stem cell-specific surface markers, were positively expressed in pluripotent stem cell-derived mesenchymal stem cells, and it was confirmed that the expression of HLA-DR, which is a cell surface marker of MEW class type II related to immune response and CD34 and CD45, which are hematopoietic stem cell-specific cell surface markers, was negative.

In addition, as a result of confirming the expression of TRA-1-60, which is a pluripotent stem cell-specific cell surface marker, in order to confirm whether the pluripotent stem cells were incorporated, it was confirmed that the prepared pluripotent stem cell-derived mesenchymal stem cells expressed specific cell surface markers of general mesenchymal stem cells by confirming that the expression of TRA-1-60 was negative (FIG. 6).

2-2: Analysis of Differentiation Ability of Mesenchymal Stem Cells

In order to analyze the differentiation ability of pluripotent stem cell-derived mesenchymal stem cells prepared by the method of Example 1, differentiation into adipocytes, osteocytes, and chondrocytes was induced for 14 days, and then each differentiation ability was verified through a specific chemical staining method.

Figure 7:
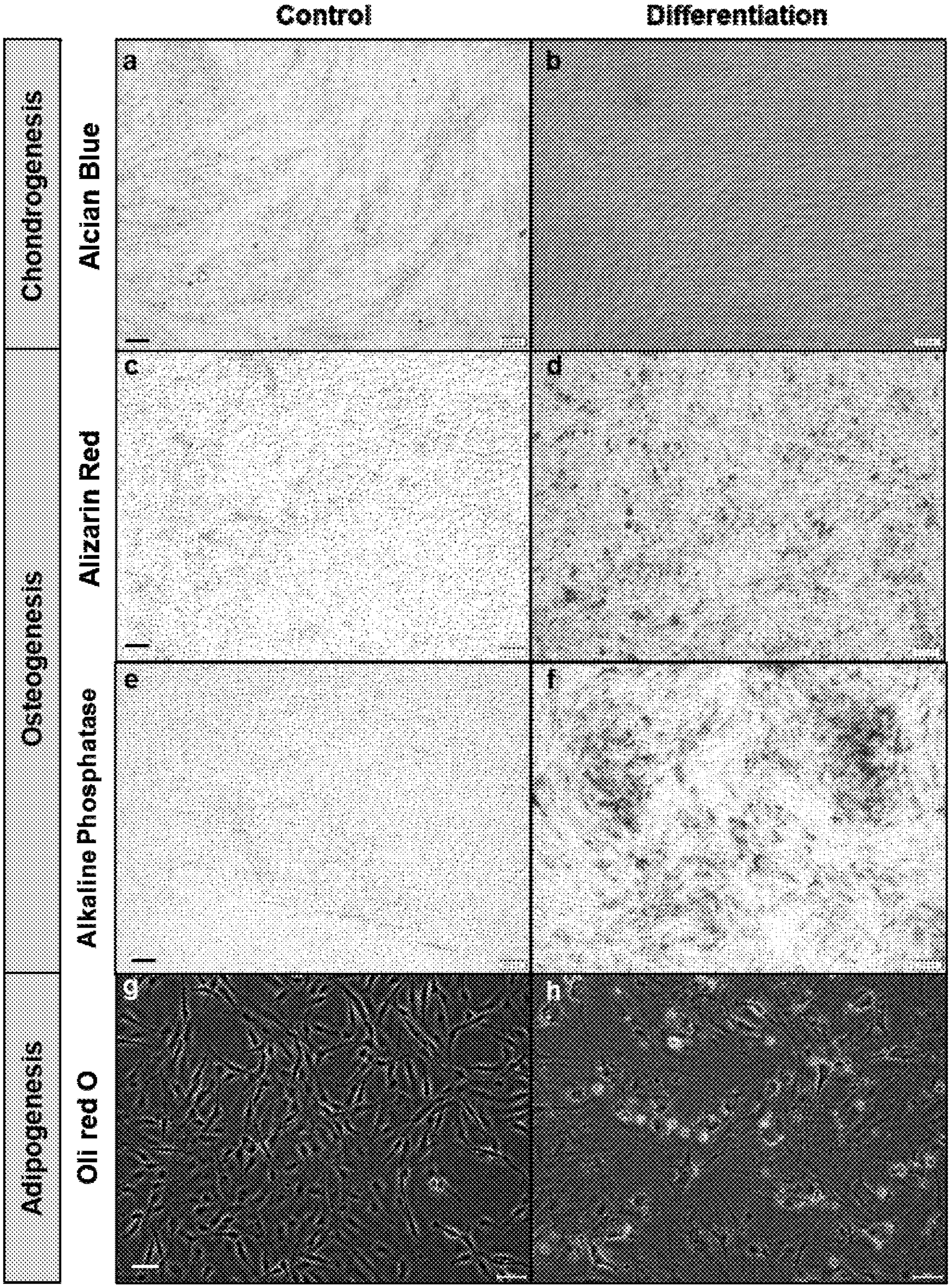
FIG. 7 illustrates the results of analyzing the differentiation ability of pluripotent stem cell-derived mesenchymal stem cells cultured in a feeder cell-free, xeno-free, and serum-free culture environment.

As a result of performing Oil-Red-0 staining after 14 days of induction of differentiation into adipocytes, it was confirmed that the prepared pluripotent stem cell-derived mesenchymal stem cells differentiated into adipocytes, and as a result of performing staining with Alizarin-Red-S and alkaline phosphatase after 14 days of induction of differentiation into osteocytes, it was confirmed that the prepared pluripotent stem cell-derived mesenchymal stem cells differentiated into osteocytes. Furthermore, as a result of performing staining with Alcian Blue after 14 days of induction of differentiation into chondrocytes, it was confirmed that the prepared pluripotent stem cell-derived mesenchymal stem cells differentiated into chondrocytes (FIG. 7).

This indicates that the pluripotent stem cell-derived mesenchymal stem cells prepared in Example 1 have a differentiation ability similar to that of general mesenchymal stem cells.

2-3: Analysis of Chromosomal Abnormalities in Mesenchymal Stem Cells

G-band karyotyping (Saccone et al, Proc Natl Acad Sci USA, 89:4913-4917, 1992) was performed to confirm whether chromosomal abnormalities occurred in the differentiation process of pluripotent stem cell-derived mesenchymal stem cells prepared by the method of Example 1.

Figure 8:
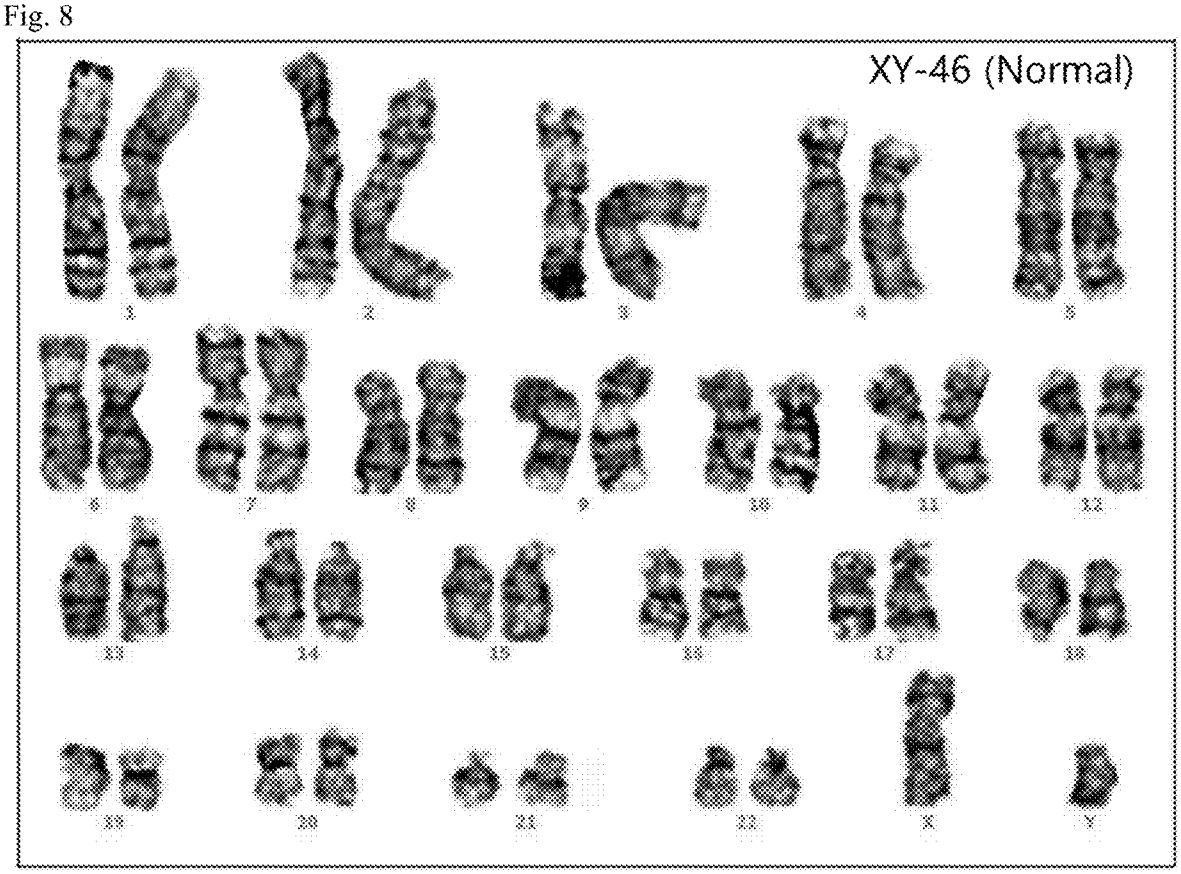
FIG. 8 illustrates the results of analyzing the G-band karyotype of pluripotent stem cell-derived mesenchymal stem cells cultured in a feeder cell-free, xeno-free, and serum-free culture environment.

As a result, a normal karyotype of 46XY was confirmed in the prepared pluripotent stem cell-derived mesenchymal stem cells, indicating that no chromosomal abnormality was caused in the differentiation process of the pluripotent stem cell-derived mesenchymal stem cells prepared in Example 1 (FIG. 8).

2-4: Analysis of Stem Cell Characteristic Persistence of Mesenchymal Stem Cells

In order to confirm the stem cell characteristic persistence (consistency) according to the subculture of pluripotent stem cell-derived mesenchymal stem cells prepared by the method of Example 1, a change in cell surface markers up to passage 20 was comparatively analyzed by performing a continuous subculture in a culture vessel.

Cell surface marker expression for mesenchymal stem cell surface markers CD29, CD44, CD73, and CD105, a hematopoietic stem cell-specific surface marker CD45, an MEW class type II marker HLA-DR, and pluripotent stem cell-specific surface markers SSEA-3, TRA-1-60 and TRA-1-81 was comparatively analyzed from passage 12 to passage 20 (Table 1).

As a result, it was confirmed that in the pluripotent stem cell-derived mesenchymal stem cells prepared by the method of Example 1, the expression of the mesenchymal stem cell surface markers CD29, CD44, CD73, and CD105 from passage 12 to passage 20 was maintained at 90% or more. In addition, it was confirmed that the expression of cell surface markers for a hematopoietic stem cell-specific surface marker CD45, an MEW class type II marker HLA-DR, and pluripotent stem cell-specific surface markers SSEA-3, TRA-1-60, and TRA-1-81 was maintained as negative.

These results suggest that the pluripotent stem cell-derived mesenchymal stem cells prepared by the method of Example 1 maintain the characteristics of mesenchymal stem cells until passage 20, and it can be said that the pluripotent stem cell-derived mesenchymal stem cells have a high utilization value as an important cellular resource for not only the mass culture of therapeutic agents using mesenchymal stem cells in the future, but also the development of cell function-strengthened stem cell therapeutic agents through gene introduction.

TABLE 1

| Marker | | Analysis results (%) PN12 | PN13 | PN14 | PN15 | PN16 |
|---|---|---|---|---|---|---|
| Identification marker | CD29 | 99.94 ± 0.03 | 98.21 ± 3.07 | 99.95 ± 0.02 | 99.84 ± 0.16 | 99.88 ± 0.03 |
| | CD44 | 99.96 ± 0.03 | 99.96 ± 0.04 | 99.97 ± 0.02 | 99.98 ± 0.00 | 99.95 ± 0.02 |
| | CD73 | 98.11 ± 0.57 | 98.85 ± 0.62 | 99.60 ± 0.04 | 99.51 ± 0.16 | 98.63 ± 1.09 |
| | CD105 | 99.64 ± 0.06 | 99.77 ± 0.26 | 99.76 ± 0.12 | 99.51 ± 0.37 | 99.27 ± 0.45 |
| Purity marker | CD34 | 2.61 ± 0.29 | 2.93 ± 1.05 | 2.07 ± 0.48 | 2.45 ± 0.17 | 1.77 ± 0.45 |
| | CD45 | 0.87 ± 0.21 | 1.18 ± 0.22 | 0.70 ± 0.21 | 0.85 ± 0.03 | 0.80 ± 0.28 |
| | HLA-DR | 0.72 ± 0.09 | 0.89 ± 0.29 | 0.75 ± 0.20 | 0.94 ± 0.24 | 0.94 ± 0.20 |
| | SSEA-3 | 0.85 ± 0.17 | 0.96 ± 0.32 | 0.69 ± 0.17 | 0.45 ± 0.26 | 0.34 ± 0.15 |
| | TRA-1-60 | 0.51 ± 0.16 | 0.44 ± 0.09 | 0.59 ± 0.14 | 0.53 ± 0.27 | 0.48 ± 0.08 |
| | TRA-1-81 | 0.59 ± 0.24 | 0.44 ± 0.07 | 0.71 ± 0.29 | 0.51 ± 0.31 | 0.32 ± 0.06 |

| Marker | | Analysis results (%) PN17 | PN18 | PN19 | PN20 |
|---|---|---|---|---|---|
| Identification marker | CD29 | 99.76 ± 0.13 | 99.78 ± 0.07 | 99.80 ± 0.13 | 99.65 ± 0.07 |
| | CD44 | 99.92 ± 0.04 | 99.89 ± 0.07 | 99.89 ± 0.02 | 99.73 ± 0.11 |
| | CD73 | 98.13 ± 0.20 | 99.13 ± 0.41 | 98.85 ± 0.73 | 99.00 ± 0.40 |
| | CD105 | 98.99 ± 0.50 | 99.49 ± 0.09 | 99.41 ± 0.28 | 99.49 ± 0.18 |
| Purity marker | CD34 | 1.52 ± 0.11 | 2.05 ± 0.79 | 1.96 ± 0.73 | 1.84 ± 0.61 |
| | CD45 | 0.82 ± 0.04 | 0.95 ± 0.17 | 1.07 ± 0.31 | 0.52 ± 0.17 |
| | HLA-DR | 0.47 ± 0.42 | 1.01 ± 0.43 | 0.88 ± 0.09 | 0.73 ± 0.21 |
| | SSEA-3 | 0.61 ± 0.20 | 0.56 ± 0.10 | 0.69 ± 0.14 | 0.80 ± 0.34 |
| | TRA-1-60 | 0.50 ± 0.06 | 0.53 ± 0.14 | 0.68 ± 0.09 | 0.44 ± 0.19 |
| | TRA-1-81 | 0.55 ± 0.06 | 0.46 ± 0.08 | 0.80 ± 0.23 | 0.49 ± 0.12 |

Example 3

Comparison of Characteristics of Pluripotent Stem Cell-Derived Mesenchymal Stem Cells According to Differences in Preparation Method 3-1: Comparison of Cell Morphology Cell morphologies of two types of pluripotent stem cell-derived mesenchymal stem cells prepared by different methods for preparing mesenchymal stem cells from the same pluripotent stem cells were compared using a microscope. A morphological comparison of passages 7 and 12 of the prepared pluripotent stem cell-derived mesenchymal stem cells was performed.

It was confirmed that the pluripotent stem cell-derived mesenchymal stem cells prepared by the existing method (WO 2011052818) and the pluripotent stem cell-derived mesenchymal stem cells prepared through the above Examples both had a spindle shape and the cell morphology was maintained similarly up to passage 7. However, in the case of pluripotent stem cell-derived mesenchymal stem cells prepared by the existing method, an aggregation phenomenon of cells occurred at passage 12.

Figure 9:
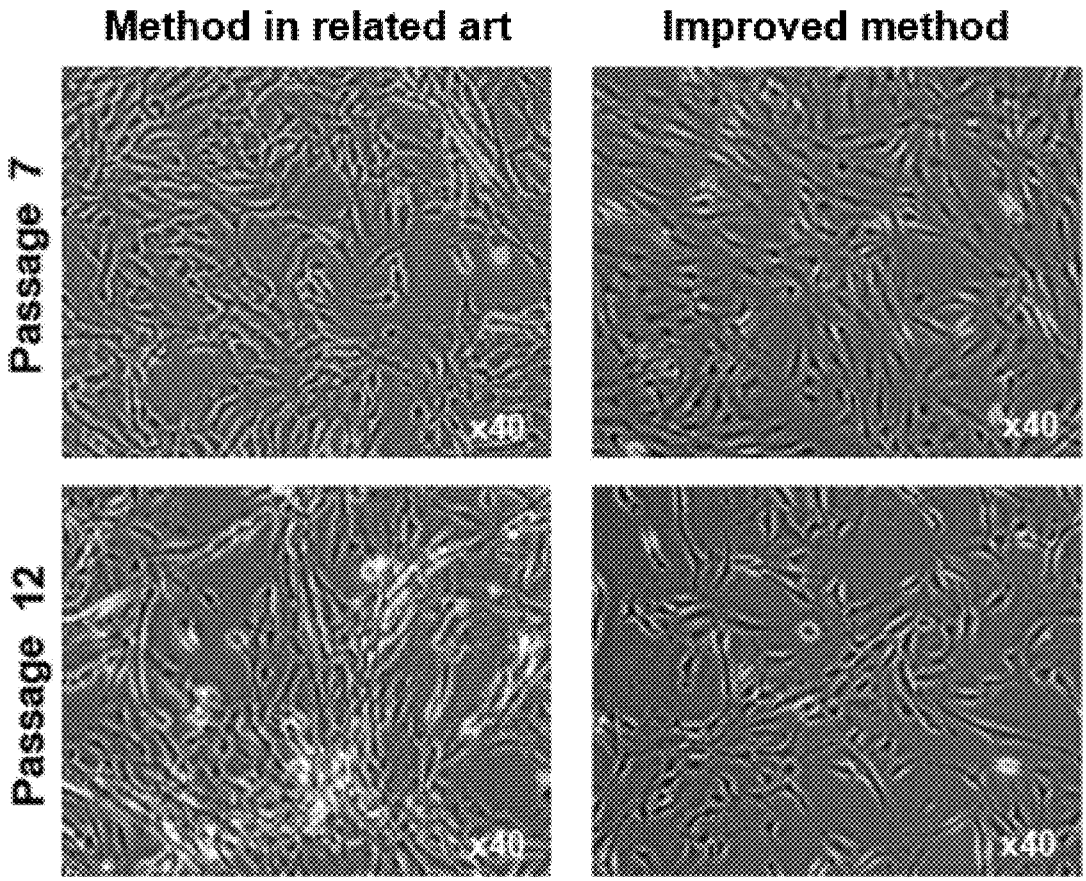
FIG. 9 compares the cell morphologies of passage 7 and passage 12 of pluripotent stem cell-derived mesenchymal stem cells prepared by the existing method for preparing mesenchymal stem cells derived from pluripotent stem cells (WO 2011052818) and pluripotent stem cell-derived mesenchymal stem cells prepared by the improved method for preparing mesenchymal stem cells derived from pluripotent stem cells of the present invention.

However, it was confirmed that the pluripotent stem cell-derived mesenchymal stem cells prepared through the above Examples well maintained the spindle-shaped cell morphology even after passage 12 (FIG. 9).

3-2. Comparison of Expressions of Cell Surface Markers

As in Example 3-1, the expressions of cell surface markers for the pluripotent stem cell-derived mesenchymal stem cells prepared by the existing method (WO 2011052818) and the pluripotent stem cell-derived mesenchymal stem cells prepared through the present invention were compared.

It was confirmed that in the pluripotent stem cell-derived mesenchymal stem cells prepared by the method of the present invention, the expression of CD29, CD44, CD73, CD105, which are mesenchymal stem cell-specific cell surface markers, was 90% or more and positive until passage 6, 8, and 12. In addition, it was confirmed that the expression of hematopoietic stem cell-specific cell surface markers CD34 and CD45, an MHC class type II marker HLA-DR, and a pluripotent stem cell-specific cell surface marker TRA-1-60 was negative (Table 2).

In contrast, in the pluripotent stem cell-derived mesenchymal stem cells prepared by the existing method, the expression of the remaining cell surface markers except for CD105 was maintained similarly to that of the pluripotent stem cell-derived mesenchymal stem cells prepared by the method of the present invention until passages 6, 8, and 12, but the expression of CD105 was found to be less than 50% in the cells of passage 6, and in particular, it was confirmed that the expression was reduced to 26.6% after passage 12 (Table 2).

TABLE 2

| Classification | Existing method (WO2011052818) PN6 | PN8 | PN12 | Improved method of present invention PN6 | PN8 | PN12 |
|---|---|---|---|---|---|---|
| CD29 | 99.9% | 100.0% | 99.9% | 99.9% | 98.6% | 99.9% |
| CD44 | 99.8% | 100.0% | 99.8% | 99.9% | 99.6% | 99.9% |
| CD73 | 99.3% | 97.9% | 97.3% | 99.9% | 99.2% | 98.4% |
| CD105 | 43.6% | 47.1% | 26.6% | 99.7% | 99.8% | 99.8% |
| CD34 | 0.9% | 2.1% | 0.8% | 6.7% | 0.7% | 1.8% |
| CD45 | 0.2% | 0.8% | 0.7% | 0.1% | 0.8% | 0.4% |
| HLA-DR | 0.5% | 0.5% | 0.2% | 0.0% | 0.9% | 0.3% |
| SSEA-3 | 0.1% | 0.0% | 0.2% | N/A | 0.4% | 0.1% |
| TRA-1-60 | 0.0% | 0.3% | 0.0% | 0.0% | 0.8% | 0.1% |
| TRA-1-81 | 0.0% | 0.4% | 0.1% | N/A | 0.8% | 0.1% |

3-3: Comparison of Abilities to Differentiate Into Osteocytes, Chondrocytes, and Adipocytes As in Example 3-1, the abilities of the pluripotent stem cell-derived mesenchymal stem cells prepared by the existing method (WO 2011052818) and the pluripotent stem cell-derived mesenchymal stem cells prepared through the present invention to differentiate into osteocytes, chondrocytes, and adipocytes were compared.

Figure 10:
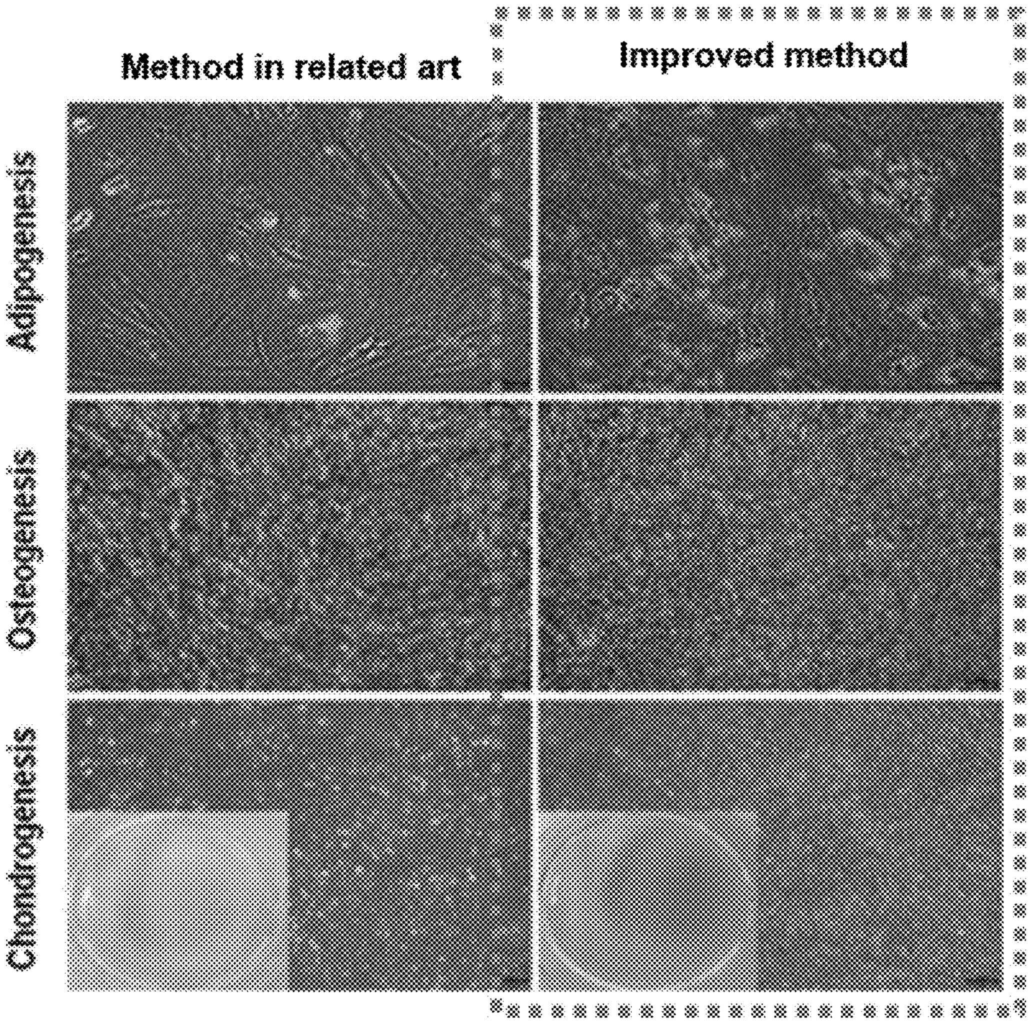
FIG. 10 confirms the ability of pluripotent stem cell-derived mesenchymal stem cells of the existing method for preparing mesenchymal stem cells derived from pluripotent stem cells (WO 2011052818) and the improved method for preparing mesenchymal stem cells derived from pluripotent stem cells of the present invention to differentiate into osteocytes, chondrocytes, and adipocytes.

It was confirmed that the pluripotent stem cell-derived mesenchymal stem cells prepared by the method of the present invention had higher differentiation ability into osteocytes, chondrocytes, and adipocytes than the pluripotent stem cell-derived mesenchymal stem cells prepared by the existing method (FIG. 10).

Example 4

Comparison of Mesenchymal Stem Cells According to Differences in Types of Pluripotent Stem Cells 4-1: Western Embryoid Stem Cell-Derived Mesenchymal Stem Cells In order to confirm whether the mesenchymal stem cells prepared by the method of the present invention differ depending on the race of origin of the pluripotent stem cells, Western embryonic stem cells (ESI-017/hES22014005, ESI-035/hES22014006) were cultured in a feeder cell-free, xeno-free, and serum-free environment.

Figure 11:
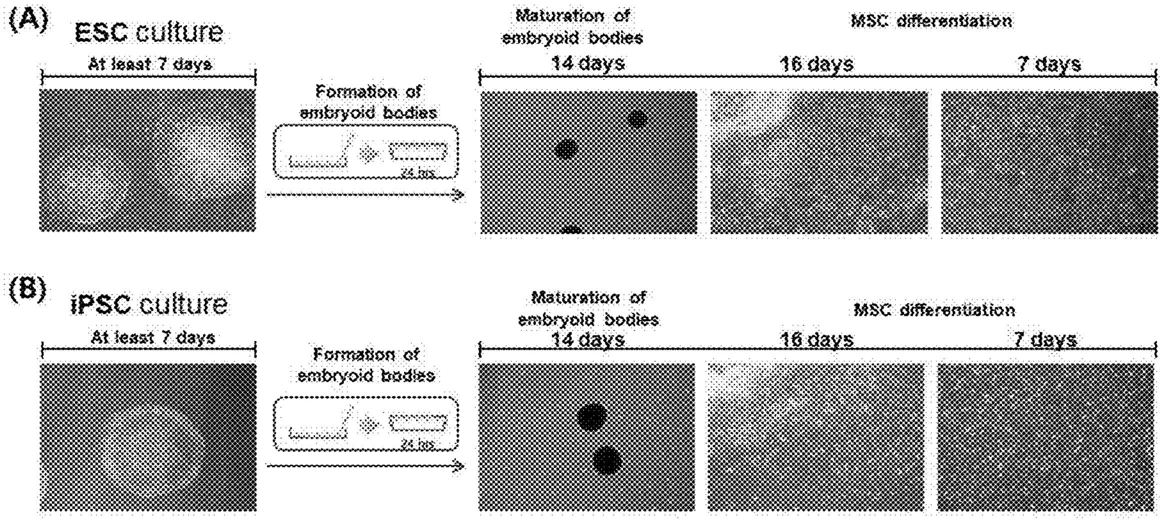
FIG. 11 is a schematic view of a method for preparing mesenchymal stem cells derived from (A) Western embryonic stem cells and (B) Asian induced pluripotent stem cells, which are cultured through the forming of the mature embryoid bodies in a feeder cell-free, xeno-free, and serum-free culture environment.

In the same manner as in Example 1-1, a tissue culture vessel was coated with human vitronectin, which is a component of human extracellular matrix, to a final concentration of 10 μg/mL, and then undifferentiated Western pluripotent stem cells were cultured using a TeSR-2 medium, which is a xeno-free and serum-free medium (FIG. 11A).

Figure 12:
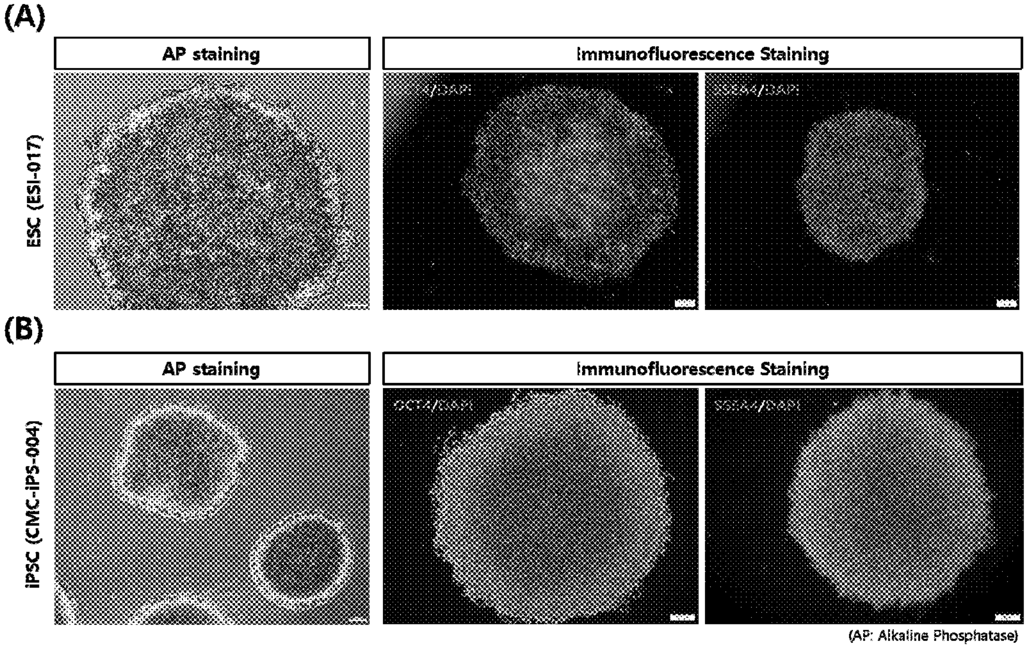
FIG. 12 analyzes the pluripotency of (A) Western embryonic stem cells and (B) Asian induced pluripotent stem cells cultured in a feeder cell-free, xeno-free, and serum-free culture environment.

As a result of confirming the expression of OCT-4 and SSEA-4, which are pluripotency markers of stem cells, through immunofluorescence staining in order to confirm the pluripotency of pluripotent stem cells cultured in a feeder cell-free, xeno-free, and serum-free environment, OCT-4 and SSEA-4 exhibiting pluripotency were expressed in the Western pluripotent stem cells. Further, it could be seen that the cultured Western pluripotent stem cells maintained pluripotency by confirming the expression of alkaline phosphatase (FIG. 12A).

In addition, in order to induce the differentiation of mesenchymal stem cells from the cultured Western pluripotent stem cells, mature embryoid bodies were formed using the same method and medium as in Example 1-2, and the mature embryoid bodies thus cultured for 14 days differentiated into mesenchymal stem cells using the same method and medium as in Example 1-3. After it was confirmed that mesenchymal stem cells differentiated from the attached mature embryoid bodies sufficiently proliferated under a microscope, the mesenchymal stem cells were subcultured, and cultured in an incubator at 37° C. and 5% $CO_2$ using a StemPro MSC SFM xeno-free medium for differentiation and proliferation in a xeno-free and serum-free environment (FIG. 11A). Therefore, it could be confirmed that the mesenchymal stem cells prepared by the method of the present invention did not differ depending on the race of origin of the pluripotent stem cells.

4-2: Induced Pluripotent Stem Cell-Derived Mesenchymal Stem Cells

In order to confirm whether the mesenchymal stem cells prepared by the method of the present invention differ depending on the types of pluripotent stem cells, induced pluripotent stem cells (iPSCs) were cultured in a feeder cell-free, xeno-free, and serum-free environment.

In the same manner as in Example 1-1, a tissue culture vessel was coated with human vitronectin, which is a component of human extracellular matrix, to a final concentration of 10 ug/mL, and then undifferentiated induced pluripotent stem cells were cultured using a TeSR-2 medium, which is a xeno-free and serum-free medium (FIG. 11B).

As a result of confirming the expression of OCT-4 and SSEA-4, which are pluripotency markers of stem cells, through immunofluorescence staining in order to confirm the pluripotency of pluripotent stem cells cultured in a feeder cell-free, xeno-free, and serum-free environment, OCT-4 and SSEA-4 exhibiting pluripotency were expressed in induced pluripotent stem cells. That is, it could be seen that the cultured induced pluripotent stem cells maintained pluripotency (FIG. 12B).

Furthermore, in order to induce the differentiation of mesenchymal stem cells from the cultured induced pluripotent stem cells, mature embryoid bodies were formed in the same manner as in Example 1-2, and the mature embryoid bodies thus cultured for 14 days differentiated into mesenchymal stem cells in the same manner as in Example 1-3. After it was confirmed that mesenchymal stem cells differentiated from the attached mature embryoid bodies sufficiently proliferated under a microscope, the mesenchymal stem cells were subcultured, and cultured in an incubator at 37° C. and 5% $CO_2$ using a StemPro MSC SFM xeno-free medium for differentiation and proliferation in a xeno-free and serum-free environment (FIG. 11B).

Therefore, it could be confirmed that the mesenchymal stem cells prepared by the method of the present invention did not differ depending on the types of pluripotent stem cells. Although specific parts of the present invention have been described in detail, it will be obvious to those skilled in the art that such a specific description is just a preferred embodiment and the scope of the present invention is not limited thereby. Therefore, the substantial scope of the present invention will be defined by the appended claims and the equivalents thereof.

INDUSTRIAL APPLICABILITY

A method for preparation of mesenchymal stem cells from human pluripotent stem cells according to the present invention employs a feeder cell-free, xeno-free, and serum-free culture environment to solve the problem of contamination with a foreign animal-derived material, the method utilizes spheroidal embryoid bodies to form mature embryoid bodies uniform in shape and size, and thus even after a long-term subculture, mesenchymal stem cells whose characteristics are not altered can be prepared in a large amount. Therefore, the invention is advantageous for commercializing cell therapeutic agents superb in safety and efficiency.

The invention claimed is:

1. A method for preparing mesenchymal stem cells from human pluripotent stem cells, the method comprising the following steps:

(a) culturing human pluripotent stem cells in a serum-free pluripotent stem cell culture medium without xeno feeder cells to obtain a colony of human pluripotent stem cells and isolating human pluripotent stem cells from the colony;

(b) forming single spheroidal embryoid bodies by suspending the isolated pluripotent stem cells in an embryoid body formation medium, and then culturing the isolated pluripotent stem cells such that pluripotent stem cells are aggregated by hanging drop culture, or culture using a V-shape tube, a round shape 96 well plate, or a conical tube;

(c) forming mature embryoid bodies by suspension-culturing the embryoid bodies in an embryoid body maturation medium for 10 to 18 days;

(d) inducing differentiation into mesenchymal stem cells by adherently culturing the embryoid bodies in a xeno-free and serum-free mesenchymal stem cell culture medium; and (e) proliferating and culturing the differentiated mesenchymal stem cells in a xeno-free and serum-free mesenchymal stem cell culture medium while maintaining the identity of mesenchymal stem cells.

2. The method of claim 1, wherein the human pluripotent stem cells are embryonic stem cells or induced pluripotent stem cells.

3. The method of claim 1, wherein the human pluripotent stem cells in Step (a) are cultured in a culture vessel coated with a material selected from the group consisting of vitronectin, collagen, laminin, Matrigel and heparan sulfate proteoglycan.

4. The method of claim 1, wherein the culture in Step (b) is performed for 18 hours to 30 hours.

5. The method of claim 1, wherein the embryoid body maturation medium in Step (c) is a basic medium comprising knock out serum replacement (KSR), non-essential amino acids (NEAA) and β-mercaptoethanol.

6. The method of claim 5, wherein the basic medium in Step (c) is DMEM/F12, alpha MEM, Ham's F12 media or DMEM.

7. The method of claim 1, wherein the mature embryoid bodies obtained in Step (c) have an average size of 350 to 450 μm.

8. The method of claim 1, wherein the mesenchymal stem cell culture medium in Steps (d) and (e) is a xeno-free and serum-free medium comprising L-glutamine.

9. The method of claim 1, wherein the induction of differentiation into mesenchymal stem cells in Step (d) is performed for 12 to 20 days.

10. The method of claim 1, wherein the mesenchymal stem cells in Step (e) are mesenchymal stem cells possessing multipotency capable of differentiating into cells selected from the group consisting of adipocytes, osteocytes, chondrocytes, myocytes, nerve cells and cardiomyocytes.

11. The method of claim 1, wherein the mesenchymal stem cells obtained in Step (e) are mesenchymal stem cells expressing CD29(+), CD44(+), CD73(+) and CD105(+) cell surface markers.

12. The method of claim 11, wherein the expression of the cell surface markers is maintained at 90% or more in mesenchymal stem cells of 20 or more passages.

13. The method of claim 1, wherein the mesenchymal stem cells obtained in Step (e) are mesenchymal stem cells of CD34(−), CD45(−), HLA-DR(−), TRA-1-60(−), and TRA-1-81(−).

* * * * *